United States Patent [19]
Moran et al.

[11] Patent Number: 6,086,363
[45] Date of Patent: Jul. 11, 2000

[54] DEVICE AND METHOD TO TREAT ORAL DISEASE IN SMALL ANIMALS

[75] Inventors: Kelly Moran; Jane Morello, both of Wilbraham, Mass.; Bill Siminovsky, Parkland, Fla.; John Stambaugh; Carol Morello, both of Wilbraham, Mass.; Kimberly Muller, Brookfield, Conn.

[73] Assignee: CeramOpter Industries, Inc., East Longmeadow, Mass.

[*] Notice: This patent is subject to a terminal disclaimer.

[21] Appl. No.: 09/195,783

[22] Filed: Nov. 19, 1998

Related U.S. Application Data

[63] Continuation of application No. 09/114,990, Jul. 14, 1998, Pat. No. 5,941,701.

[51] Int. Cl.⁷ .................................................. A61D 5/00
[52] U.S. Cl. ............................ 433/1; 433/215; 433/141; 433/29; 606/2; 606/15
[58] Field of Search ................................ 433/1, 215, 29, 433/216, 226, 229, 141; 606/2, 3, 10, 15, 16, 14, 13; 128/898

[56] References Cited

U.S. PATENT DOCUMENTS

| | | |
|---|---|---|
| 4,940,411 | 7/1990 | Vassiliadis et al. ..................... 433/215 |
| 5,382,163 | 1/1995 | Putnam ..................................... 433/215 |
| 5,388,987 | 2/1995 | Badoz et al. ............................... 433/29 |
| 5,409,376 | 4/1995 | Murphy ..................................... 433/29 |
| 5,474,449 | 12/1995 | Loge et al. ................................. 433/29 |
| 5,611,793 | 3/1997 | Wilson et al. ............................... 606/2 |
| 5,616,141 | 4/1997 | Cipolla ..................................... 606/15 |
| 5,636,983 | 6/1997 | Shoji et al. ............................... 433/29 |
| 5,658,148 | 8/1997 | Neuberger et al. ...................... 433/215 |
| 5,941,701 | 8/1999 | Moran et al. ............................... 433/1 |

*Primary Examiner*—Gene Mancene
*Assistant Examiner*—Philogene Pedro
*Attorney, Agent, or Firm*—Bolesh J. Skutnik; B J Associates

[57] ABSTRACT

A laser system and method are described that will improve dental treatments in small animals, particularly in situations where periodontal disease has progressed to the advanced stages of periodontitis and when dental pulp is exposed by fracture or disease. A laser system is employed to achieve enhanced precision by selectively ablating affected tissue without damaging the collateral tissue. The laser system is also capable of sealing the tubules and eradicating bacteria within the periodontium to significantly reduce the risk of infection. Additional pre-treatment methods may be employed to further enhance the laser therapy.

20 Claims, 3 Drawing Sheets

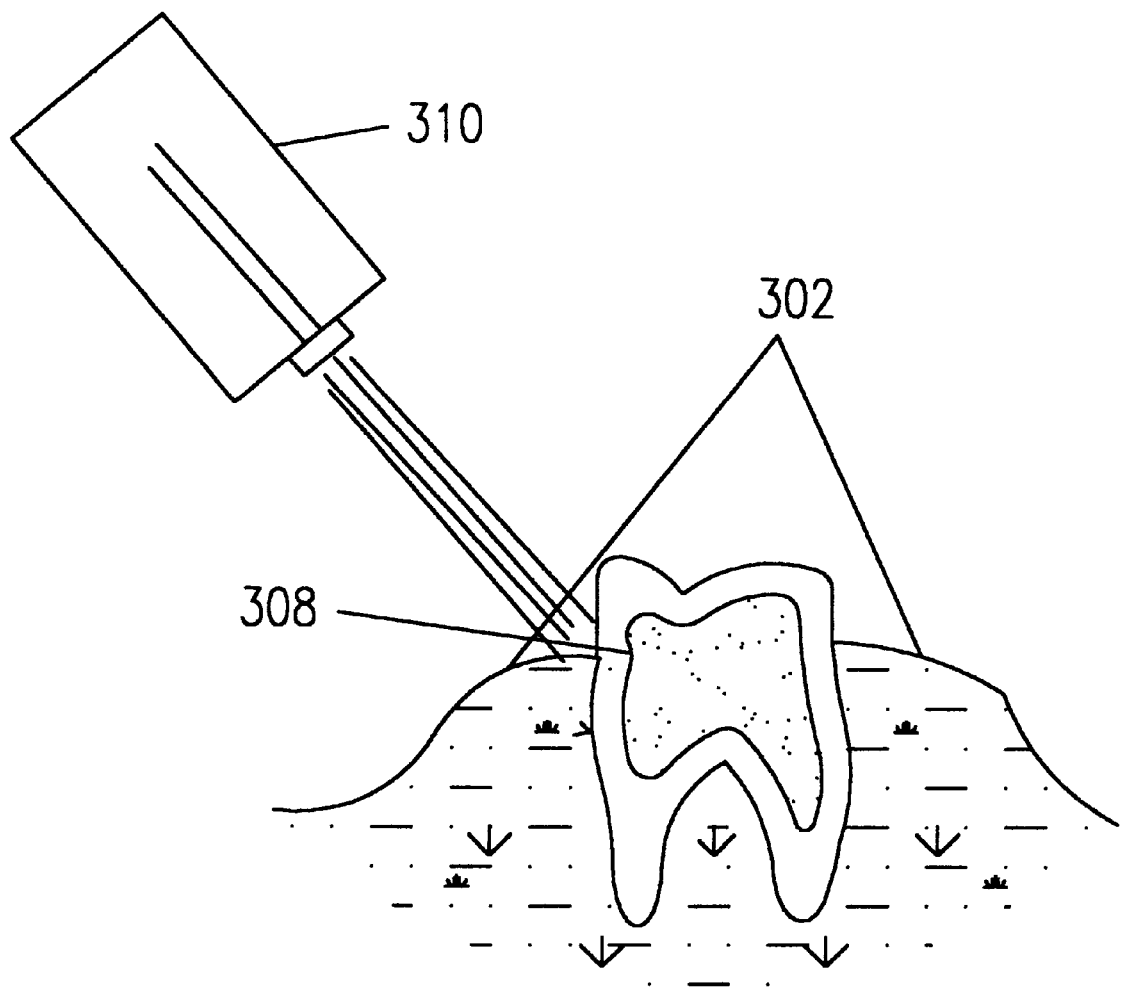

DEVICE AND METHOD TO TREAT ORAL DISEASE IN SMALL ANIMALS

REFERENCE TO RELATED CASE

This application is a continuation of Patent Application 09114-990 filed on Jul. 14, 1998 by Kelly Moran et al, inventors, entitled "A DEVICE AND METHOD TO TREAT ORAL DISEASE IN FELINES," and incorporated by reference herein now U.S. Pat. No. 5,941,701.

BACKGROUND OF THE INVENTION

1. Field of the Invention

The present invention relates to a device and method to improve dental treatments in small animals, particularly in situations where periodontal disease has progressed to the advanced stages of periodontitis and when dental pulp is exposed by fracture or disease.

2. Background of the Invention

Periodontal disease is especially prevalent in small animals. Periodontal disease can range from a localized inflammation of the gingiva (gingivitis) to inflammation of the gingiva, alveolar bone, the periodontal ligament and tooth structure (periodontitis).

Generally, the protocol for treating periodontal disease focuses on cleaning the oral cavity, repairing the tissue, and stopping the progression of the disease. However, available treatment methods, which include scalping, polishing, curettage, dental extractions, root planing, gingivectomies, and in extreme cases, gingival flaps or grafts are inadequate when treating advanced periodontitis.

Root planing is often necessary to remove necrotic tissue from the roots of periodontally involved teeth. A currette or Orban file is applied to the root surface and withdrawn in overlapping strokes using sufficient pressure to scrape necrotic cementum and debris from the root and smooth its surface. However, it is difficult to remove the necrotic debris without affecting the surrounding soft tissue.

A gingivectomy is often performed to eliminate gingival sulcus, in an effort to facilitate plaque control and oral hygiene. A gingivectomy is required where pocket depths exceed 4 mm, the epithelial attachment is still above bone level, and resection can be contained within the attached gingiva. The level of epithelial attachment is determined by using a periodontal probe and is marked on the buccal surface of the gingiva. The gingival tissue is then excised using a periodontal knife. Digital pressure is usually sufficient to effect hemostasis. However, it is difficult to limit resection to the attached gingiva. Additionally, the working space is limited in smaller breeds restricting maneuverability of instruments within the mouth thereby reducing the precision by which the procedure can be performed.

Cats exhibit particular manifestations of periodontal disease that are unique to the feline species. For example, a chronic problem in cats that is commonly associated with both chronic gingivitis/periodontitis and feline lymphocytic-plasmacytic stomatitis is external root resorption. Inflammatory resorption occurs at the cementoenamel junction. The presence of exuberant gingival tissue often conceals extensive cavitations in the tooth that undermine the crown eventually causing it to fracture and crumble thereby exposing the dentin. Exposed dentin is sensitive and extremely painful.

Typically, a fluoride gel is administered to treat this condition to desensitize the dentin. However, restoration has not been very successful and in many circumstances all of the teeth must be extracted. Extraction of involved teeth is often difficult because the crowns are weakened and therefore tend to fracture easily. Additionally, the roots are usually ankylosed and hard to separate from the surrounding bone. The long-term therapeutic response for treating external root resorption has typically been poor.

The cats are also placed on systemic antibiotics and long-term corticosteroids to reduce the risk of infection and to reduce inflammation. However, antibiotic treatments are usually not effective in treating feline lymphocytic-plasmacytic gingivitis/stomatitis because a primary bacterial causative agent has not yet been identified.

Tooth fracture is especially prevalent in canines. Cats tend to be more fastidious in their diet and occlusal habits, therefore, fractures of teeth are less common in cats than in dogs. A root canal is the conventional treatment method for tooth fractures. When the dental pulp is exposed by fracture or other disease, pulp contamination and necrosis will result in eventual resorption of supporting bone around the root apex as well as periapical abscessation or cyst formation. This process will result in eventual tooth loss. Endodontic therapy (root canal procedure) can be performed in order to ensure retention of an endodontically involved tooth. Endodontic treatment involves using a endodontic file to file away part of the contents or wall of the pulp canal. The enlarged canal is then sterilized with alternating flushes of hypochlorite (bleach) and hydrogen peroxide solutions and flushed with a sterile saline. The sterile canal is then dried and filled with root canal cement and one or more gutta percha points compressed in place. However, if the tooth is not sealed perfectly, bacteria present at the time of the procedure, can lead to pulpal necrosis and abscess formation.

Thus there is a need for a device and method that will improve dental treatment for small animals with periodontal disease and pulp exposure without the complications associated with the prior art.

OBJECTS AND SUMMARY OF THE PRESENT INVENTION

It is an object of the present invention to provide a laser system and treatment method that will eliminate the complications associated with the prior art.

It is another aim of the present invention to eliminate the chronic symptoms associated with periodontal disease in small animals.

It is further aim of the present invention to employ a laser system to achieve enhanced precision in surgical procedures.

It is an even further aim of the present invention to seal the tubules in the surrounding tissue to eradicate bacteria to significantly reduce the risk of infection.

Briefly stated, the present invention describes a laser system and method that will improve dental treatments in small animals, particularly in situations where periodontal disease has progressed to the advanced stages of periodontitis and when dental pulp is exposed by fracture or disease. A laser system is employed to achieve enhanced precision by selectively ablating affected tissue without damaging the collateral tissue. The laser system is also capable of sealing the tubules and eradicating bacteria within the periodontium to significantly reduce the risk of infection. Additional pre-treatment methods may be employed to further enhance the laser therapy.

BRIEF DESCRIPTION OF THE EMBODIMENTS

FIG. 1 Graph depicting $H_2O$ absorption spectra in the wavelength of interest.

FIG. 2 Cross-section of mandibular molar afflicted with external root resorption.

FIG. 3 Schematic view of laser system used to treat feline lymphocytic-plasmacytic gingivitis/ stomatitis.

DETAILED DESCRIPTION OF THE PREFERRED EMBODIMENT(S)

The present invention describes a new device and method to improve dental treatments in small animals, particularly in situations where periodontal disease has progressed to the advanced stages of periodontitis and when dental pulp is exposed by fracture or disease.

A preferred embodiment of the present invention employs a 980 nm diode laser to achieve high precision, low penetration cutting while simultaneously eradicating bacteria within the periodontium to significantly reduce the risk of infection.

Figure 1:
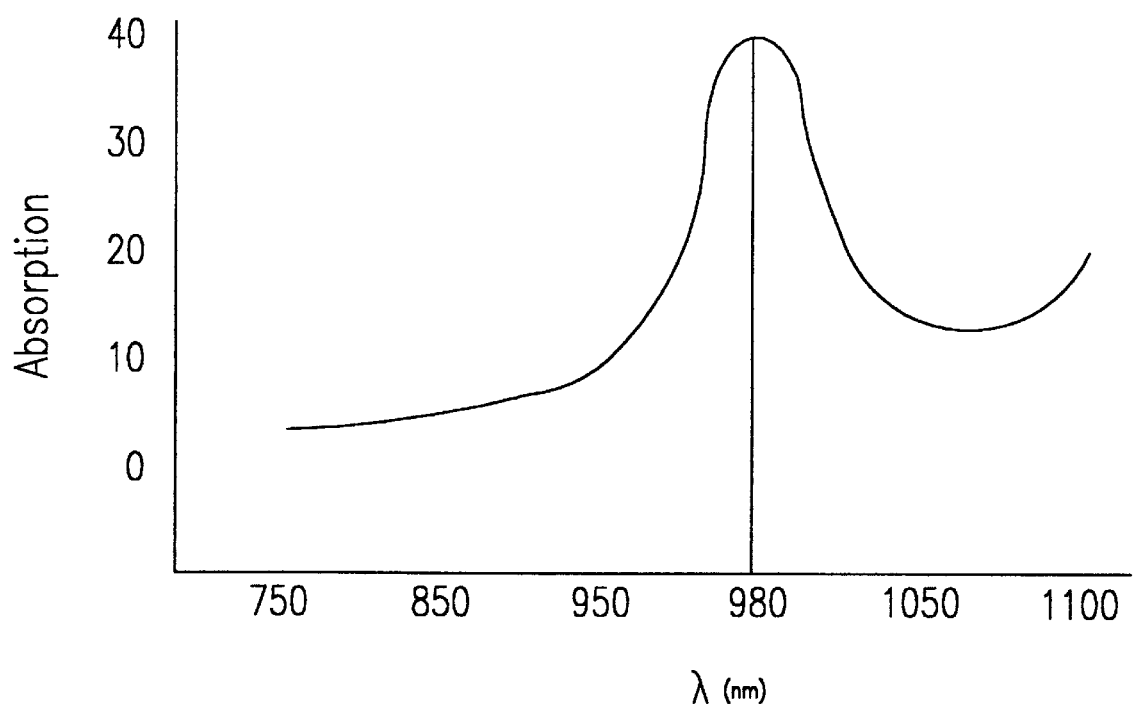

In FIG. 1, the absorption spectra of water illustrates a peak in the vicinity of 980 nm indicating that 980 nm light is well absorbed by water. The absorption exhibits a valley in the 1064 nm range indicating that only moderate absorption can be achieved by lasers employing 1064 nm light. Thus, 980 is preferred over 1064 nm for medical procedures involving soft tissue because greater absorption leads to high precision, low penetration cutting.

In an example and preferred embodiment of the present invention, a 980 nm diode laser may be used to perform a gingivectomy on a canine with idiopathic gingival hyperplasia. Idiopathic gingival hyperplasia results in an increase in the depth of the gingival sulcus. A gingevectomy will eliminate the gingival sulcus, in an effort to facilitate plaque control and oral hygiene. A gingivectomy is a preferred treatment option when pocket depths exceed 5 mm, the epithelial attachment is still above bone level, and resection can be contained within the attached gingiva.

The level of epithelial attachment is determined by using a periodontal probe and is marked on the buccal surface of the gingiva. The 980 nm diode laser is then employed to resect the excess gingival tissue and to eradicate bacteria within the treatment site. A 200–1000 µm optical fiber is employed to transport and direct radiation to the affected tissue in a continuous mode. A small spot size is generally preferred to concentrate high amounts of energy into the tissue to achieve rapid vaporization. Typically, 1–3 watts of power are applied to the periodontium to resect the necrotic tissue.

After the resection, the laser can then operate in a pulsed mode to seal the tubules thereby preventing the osmotic action of the tubules from replanting bacteria, present at the time of the procedure, into the newly grown tissue.

One of ordinary skill in the art, in light of teachings herein, can readily use this method to perform similar surgical procedures that require ablation of affected oral tissue to treat periodontal disease in small animals without exceeding the scope of this invention. An example would include using the present invention to perform a root planing procedure in which a 980 nm diode laser would be used instead of a curette or Orban file to remove necrotic cementum and debris from the roots of periodontally involved teeth.

Figure 2:
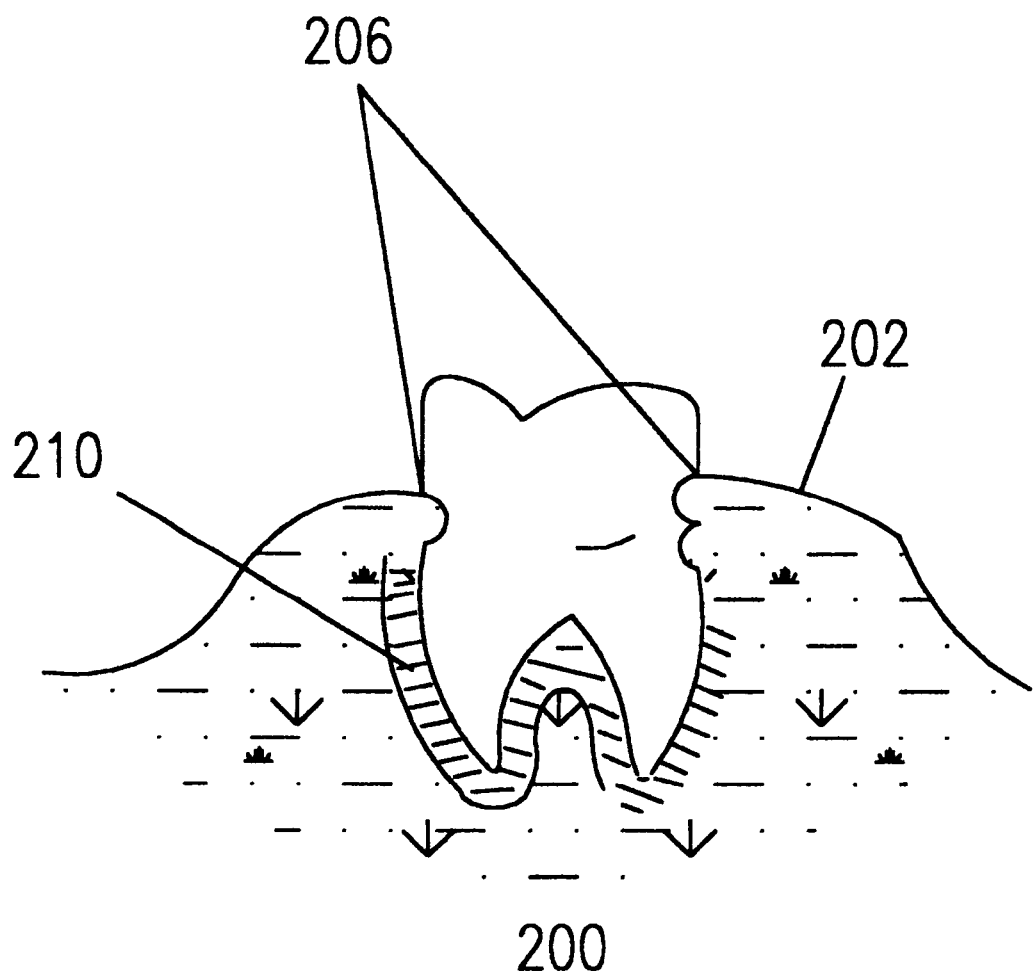

FIGS. 2 and 3 illustrate another example and preferred embodiment in which the present invention was used to treat feline lymphocytic-plasmacytic stomatitis. Feline lymphocytic-plasmacytic stomatitis (also known as feline plasma cell gingivitis-pharyngitis and chronic feline gingivitis-stomatitis) is an oral disease of unknown etiology that is frequently encountered in cats. Cats with feline lymphocytic-plasmacytic stomatitis have proliferative and ulcerated gingiva that extends into the soft palate and oropharnyx. The gingiva may recede, there may be bone loss, the roots may become exposed, and abscesses may form. Cats with feline lymphocytic-plasmacytic stomatitis suffer from intense oral pain that is typically attributable to external root resorption.

FIG. 2 is a cross-sectional view of a mandibular molar that is afflicted with external root resorption. The presence of exuberant gingival tissue 202 conceals extensive cavitations 206 in tooth 200 that undermines crown 210 eventually causing it to fracture and crumble. In typical current treatments, tooth 200 would be extracted. Generally, the response to extractions is favorable. However, extractions are not always successful for treating external root resorption when the cat has feline lymphocytic-plasmacytic stomatitis. Approximately 20% of the cats with feline lymphocytic-plasmacytic stomatitis experience a relapse following the extraction and the long-term response is typically poor.

FIG. 3 shows a preferred embodiment of the present invention in which a 980 nm diode laser 310 was used to treat a cat with feline lymphocytic-plasmacytic stomatitis who had relapsed following extraction. Laser 310 was set to deliver an optical power of 2 W to resect gingiva 302 to the cementoenamel junction 308 and effectively eliminate the affected tissue and eradicate bacteria in the periodontium. A 600 µm flat tip optical fiber 304 directs radiation to the affected tissue in a continuous mode. A small spot size was used to concentrate high amounts of energy into the tissue to achieve rapid vaporization.

After the resection, the laser was then set to 1 W (pulsed 1 sec on/ 1 sec off) to seal the tubules thereby preventing the osmotic action of the tubules from replanting bacteria, present at the time of the procedure, into the newly grown tissue.

In yet another example and preferred embodiment of the present invention, a diode laser system with multi-wavelength sources may be employed in conjunction with a photosensitizer to stop the progression of periodontitis in small animals. Generally, 980 nm light may be employed to resect the affected tissue and a wavelength that is suitable to activate the photosensitizer may be used to eradicate the gram-negative bacteria in the periodontium.

The photosensitizer liquid or paste, when activated by an appropriate laser wavelength, produces hyperactive singlet oxygen that are capable of destroying bacteria. The oxygen singlets will destroy the gram-negative bacteria that are reacting with the inflammatory cells in the periodontium to mediate the inflammatory response. Specifically, the plasma cells elaborate antibodies against endotoxins, produced by the gram-negative bacteria, thereby producing antigen-antibody complexes that activate the complement system of the cat. The result of complement activation is the production of biologically active substances such as anaphylatoxins, which mediate various aspects of the inflammatory response. By eradicating the gram-negative bacteria, the antigen-antibody complex that is responsible for activating the complement system is effectively destroyed, therefore, the inflammatory response is not initiated thereby effectively interrupting the chronic progression of the disease.

Particular pre-treatment methods can be especially advantageous in treating periodontitis when used in conjunction with the present laser system. The laser treatment may be preceded by mechanically cleansing the surface of the teeth and by disinfecting the oral cavity with an antiplaque substance to remove the gram-negative bacteria on the surface of the teeth. Antimicrobial agents such as chloramphenicol, clindamycin, tetracycline or metronidazole may also be of some benefit prior to the dental procedure in certain circumstances where the canine's immune system is suppressed. The photosensitizer may then be applied to the periodontium and a multi-wavelength laser system can be employed to activate the photosensitizer and to resect necrotic tissue at the roots of the periodontially involved teeth to eliminate the chronic symptoms associated with the condition. Additionally, the tubules may be sealed to further reduce the risk of infection.

In yet another example, the present invention may be used to improve endodontic therapy. The 980 nm diode laser is capable of making bloodless incisions under aseptic conditions with no mechanical contact with the target tissue to sever the dental pulp by laser without hemorrhage, mechanical damage or bacterial contamination. For example, when the dental pulp is exposed following a fracture or disease, the pulp exposure (fracture site) may be enlarged with a burr in a dental handpiece. The 980 nm diode laser may then be employed to ablate the necrotic pulp tissue while simultaneously sterilizing the canal with the laser's radiation. A color change indicates that the canal is properly prepared and ready to be filled with root cement and sealed at the crown end with amalgam.

One of ordinary skill in the art, in light of teachings herein, can readily use this method to perform other endodontic procedures without exceeding the scope of this invention. An example would include using the present invention to reduce dentin permeability or to remove residual tissue down to the apex following a root canal.

Although most references cite to a laser employing 980 nm light, this should not be taken to imply that the present invention is limited to using 980 nm light. Any wavelength that is capable of achieving high precision, low penetration cutting may be used without departing from the scope of the present invention.

Certain other changes may be made in the above constructions without departing from the scope of the present invention, it is intended that all matter contained in the above description and shown in the accompanying drawings be considered as illustrative and not in a limiting sense. For example, a desired energy choice may include, but is not limited to radiation from flashlamps, diode, frequency doubled laser diodes, laser diode pumped lasers, or photoluminescent diodes without departing from the scope of the present invention.

Having described the preferred embodiments of the present invention with reference to the accompanying drawings, it is to be understood that the invention is not limited to these precise embodiments, and that various changes and modifications may be effected therein by one skilled in the art without departing from the scope or spirit of the invention as defined in the appended claims

What is claimed is:

1. A laser system for treating periodontal disease in small animals comprising:

a diode laser having an operating wavelength which is absorbed by small animal oral tissue to achieve high precision, low penetrating cutting; wherein said operating wavelength can resect affected tissue and seal tubules;

means to transport laser radiation of said wavelength from said laser to said small animal oral tissue; and means of reducing risk of infection in said small animal oral tissue.

2. A laser system according to claim 1 wherein said laser is operating at a wavelength absorbed by water moieties at approximately 980 nm.

3. A laser system according to claim 1, wherein said laser has a multi-wavelength source that can resect affected tissue and seal tubules with one wavelength and can activate a photosensitizer with another wavelength.

4. A laser system according to claim 1, wherein said means to transport radiation is at least one optical fiber.

5. A laser system according to claim 1, wherein said laser radiation is delivered in a continuous mode to said oral tissue.

6. A laser system according to claim 1, wherein said laser radiation is delivered in a pulsed mode to said oral tissue.

7. A laser system according to claim 1 wherein said means of reducing risk of infection is a sealing of tubules to prevent microbial invasion, during and after treatment.

8. A treatment method for treating periodontal disease in small animals comprising the steps of:

positioning a laser having an operating wavelength which is absorbed by small animal periodontal tissue, wherein said operating wavelength can resect affected tissue and seal tubules;

connecting to said laser, means to transport laser radiation to said small animal periodontal tissue; and irradiating said periodontal (oral) tissue with radiation from said laser to resect affected tissue and to seal tubules to reduce risk of infection.

9. A treatment method according to claim 8 wherein said affected tissue is gingiva and it is resected to the cementoenamel junction.

10. A treatment method according to claim 8 wherein a second wavelength is added, one that will activate a photosensitizer, which can produce hyperactive singlet oxygen to further reduce risk of infection.

11. A treatment method according to claim 10 further comprising steps of:

applying a photosensitizer to said small animal periodontal tissue prior to irradiation by said laser; and activating said photosensitizer with said laser's second wavelength.

12. A treatment method according to claim 8, further comprising pre-treatment steps of:

mechanically cleansing teeth to remove plaque containing gram-negative bacteria; and disinfecting an oral cavity with an antiplaque substance.

13. A treatment method according to claim 12, further comprising a step of:

administering antibiotics to systemically ill animals prior to laser therapy.

14. A treatment method according to claim 11 wherein said affected tissue is gingiva and it is resected to the cementoenamel junction.

15. A treatment method according to claim 14, further comprising pre-treatment steps of:

mechanically cleansing teeth to remove plaque containing gram-negative bacteria; and disinfecting an oral cavity with an antiplaque substance.

16. A treatment method according to claim 15, further comprising a step of:

administering antibiotics to systemically ill animals prior to laser therapy.

17. A treatment method according to claim 9, further comprising pre-treatment steps of:

mechanically cleansing teeth to remove plaque containing gram negative bacteria; and disinfecting an oral cavity with an antiplaque substance.

18. A treatment method according to claim 17, further comprising a step of:

administering antibiotics to systemically ill animals prior to laser therapy.

19. A treatment method according to claim 11, further comprising pre-treatment steps of:

mechanically cleansing teeth to remove plaque containing gram-negative bacteria; and disinfecting an oral cavity with an antiplaque substance.

20. A treatment method according to claim 19, further comprising a step of:

administering antibiotics to systemically ill animals prior to laser therapy.

* * * * *